United States Patent [19]
Haslimann

[11] Patent Number: 5,821,113
[45] Date of Patent: Oct. 13, 1998

[54] METHOD OF REDUCING CONTAMINATION AND COMPOSITION FOR USE IN THE METHOD

[75] Inventor: Artur Haslimann, Shenstone, United Kingdom

[73] Assignee: Envorflow Inc., Manassas, Va.

[21] Appl. No.: 610,080

[22] Filed: Feb. 29, 1996

Related U.S. Application Data

[63] Continuation of Ser. No. 116,119, Sep. 2, 1993, abandoned.

[30] Foreign Application Priority Data

May 25, 1993 [GB] United Kingdom .................. 9310770

[51] Int. Cl.⁶ ................................. B09B 3/00; C02F 3/34
[52] U.S. Cl. .......................... 435/264; 210/601; 210/606; 210/610; 210/611; 210/922; 435/262; 435/262.5; 435/281; 501/101
[58] Field of Search ................................. 435/262, 262.5, 435/281, 282, 264; 588/261, 901; 210/600, 601, 606, 611, 610, 922; 507/90, 100, 101

[56] References Cited

U.S. PATENT DOCUMENTS

| | | | |
|---|---|---|---|
| 3,959,127 | 5/1976 | Bartha et al. ........................... | 210/610 |
| 4,087,356 | 5/1978 | Marconi et al. ......................... | 210/610 |
| 4,146,470 | 3/1979 | Mohan et al. ........................... | 210/601 |
| 4,415,661 | 11/1983 | Thirumalachar et al. .............. | 435/174 |
| 4,415,662 | 11/1983 | Thirumalachar et al. .............. | 435/176 |
| 4,521,515 | 6/1985 | Hata ....................................... | 435/248 |
| 4,535,061 | 8/1985 | Chakrabarty et al. ................. | 435/252.4 |
| 4,591,443 | 5/1986 | Brown et al. ........................... | 210/747 |
| 4,853,334 | 8/1989 | Vandenbergh et al. ................. | 435/262 |
| 4,859,594 | 8/1989 | Porter .................................... | 435/172.1 |

OTHER PUBLICATIONS

Sicher et. al. "Orbans Oral Histology & Embryology" pp. 269–297. 1972.

*Primary Examiner*—Nancy Degen
*Attorney, Agent, or Firm*—Webb Ziesenheim Bruening Logsdon Orkin & Hanson, P.C.

[57] ABSTRACT

Contamination by organic materials is treated by applying an aqueous composition comprising organisms which are useful in degradation of the contaminant, a nutrient for the organisms and a polymer which is soluble in or dispersible in the water and which increases the viscosity of the composition. The composition is useful in the treatment of contaminated liquids and solids and in the protection of solid surfaces against contamination.

15 Claims, No Drawings

METHOD OF REDUCING CONTAMINATION AND COMPOSITION FOR USE IN THE METHOD

This is a continuation of application Ser. No. 08/116,119 filed on Sep. 2, 1993, now abandoned.

BACKGROUND TO THE INVENTION

The present invention relates to the use of organisms to reduce contamination.

Organisms, for example bacteria, are useful in reducing contamination by a variety of contaminants. For example, there are known bacteria capable of degrading hydrocarbons by their oxidation or partial oxidation to form carbon dioxide and water. There are known respective organisms which are useful in dealing with a wide variety of contaminants.

It is known to mix bacteria with water, to facilitate distribution of the bacteria onto a contaminant. It is also known to mix bacteria with a solid, for example porous granules, to facilitate distribution of the bacteria onto a contaminant.

In many situations involving contamination, organisms are not very effective in reducing the contamination because the organisms themselves and/or enzymes which they produce are dispersed too readily from the contaminant.

SUMMARY OF THE INVENTION

According to a first aspect of the present invention, there is provided an aqueous composition comprising organisms useful in the degradation of organic material, a nutrient for the organisms and a thickening agent capable of increasing the viscosity of water. We have found that such a composition enables the organisms to be used more effectively than is the case when organisms are dispersed with nutrients only in water. The composition is found to protect, to some degree, the organisms against a hostile environment, for example an environment containing materials which are toxic to the organisms. The thickening agent impedes migration of the organisms and/or enzymes produced thereby from a contaminant to which the composition is applied.

The degree of thickening of the composition is selected according to the circumstances in which the composition is to he used and according to the time for which the composition is required to remain where it has been applied. Generally, it is desirable that, once the contamination has been removed, the composition will disperse.

In a case where the composition is required to remain on a contaminated vertical surface for a period sufficient to remove the contamination, then a composition which is more viscous than a composition suitable for application to an upwardly facing, horizontal surface may be suitable. Also, in a case where the composition is to be applied to the surface of a solid which is subjected to rapidly moving water, a relatively viscous composition may be advantageous.

A polymer which is dispersible in or soluble in water is a suitable thickening agent. Organic polymers are preferred. Polysaccharides are suitable.

The thickening agent is preferably non-ionic. The thickening agent may be selected to provide that the viscosity of the composition will increase when the composition is left exposed to the ambient atmosphere and is undisturbed. The composition may be such that it will form a flexible but substantially solid skin on a surface. However, the composition is required to remain permeable to water and to air, in order that the organisms can be sustained in an active condition at the interface between the composition and the contaminant.

The invention also comprises a variety of applications of the composition, examples of which are mentioned hereinafter.

The organisms incorporated in the composition are selected for their ability to degrade the particular contaminant on which the composition is to be used. Numerous strains of suitable organisms are known. There is also incorporated in the composition an appropriate nutrient or mixture of nutrients to promote growth and reproduction of the organisms.

The invention may be used in the treatment of any pollutant for which there are available now or become available organisms useful in degradation or other treatment of the pollutant.

DESCRIPTION OF SELECTED EMBODIMENTS

One example of a suitable composition comprises an aqueous solution of hydroxypropyl methyl cellulose. The composition contains up to 10% by weight of selected organisms, together with an appropriate proportion of nutrient for the organisms. The proportion of the cellulose-based polymer present in the solution is selected according to the intended use of the composition. A composition which is to be sprayed onto a solid surface may comprise 0.2% by weight of the polymer. In a case where the composition is to be injected into a mass of material, the composition may comprise up to 10% polymeric material, by weight. A suitable polymeric material is that sold by Courtaulds Fibres Limited under the designation Celacol HPM15000DS. This has a molecular weight distribution such that a 2% aqueous solution at 20° C. has a viscosity in the region of 13,000 to 17,000 cp. The polymeric material may be supplied as a powder containing up to 10% water and be mixed with the required amount of water. The organisms may be provided in admixture with the nutrient or nutrients in the form of an aqueous paste or a dispersion in water and the required weight of this paste or dispersion is added to the aqueous solution of the polymer. Alternatively, the organisms and nutrient may be mixed with the water before the polymer is added.

The composition may be injected into a mass of particulate material, for example soil, at a number of positions to form a substantially continuous region containing the composition. This acts as a barrier to restrict migration through the mass of material of a contaminant which is degraded by the organisms in the composition. For example, in a case where the ground has been contaminated with oil, the composition may be injected in an annular region around the periphery of the contaminated region to prevent spread of the oil beyond that region. The contaminated region may then he treated by injection of the composition into the contaminated region or in other ways, for example by excavation and incineration of the soil. We have found that the activity of the organisms in respect of oil is prolonged by the presence of the polymeric material. This may be partly because the polymeric material prevents the organisms and nutrient being leached from the region into which they are injected and partly because the polymeric material protects the organisms against toxins present in the soil.

The composition may also be applied to a contaminated surface. This may be the surface of a body of water, for example the sea, or of an aggregation of particles, for example, the ground, or the surface of an integral, solid body, for example a pebble, a rock, a harbour wall or other structure which is contacted by the sea, the wall of a building or of a tank. The composition is useful in the cleaning of tanks which have been used for the storage of oil. Accumulations of substantially solid materials adhere to the walls of oil tanks and must be removed occasionally. A composition according to the present invention can be applied to such accumulations by spraying or by means of a brush or roller and will adhere to inclined and even vertical surfaces so that the organisms are held in close proximity to the accumulation on the wall of the tank. Substances produced by the organisms and which attack the hydrocarbons in the accumulation will be present continuously at the interface between the accumulation and the applied composition. This achieves effective emulsification of the hydrocarbons and converts the accumulation into a flowable condition. The accumulated matter will then flow to the bottom of the tank and can be removed by pumping.

In a case where the external wall of a building is contaminated by hydrocarbons, the application and action of a composition embodying the present invention will be similar to that in the case of an oil tank but when the contaminating hydrocarbons have been degraded to a flowable condition, they will be washed from the wall. Alternatively, the composition embodying the present invention may be maintained in contact with the hydrocarbons until they are substantially oxidised. The composition embodying the present invention is not readily permeable to hydrocarbons. Accordingly, the hydrocarbons which were present in substantially solid hydrocarbon contamination but which have been emulsified by the applied organisms will be trapped by the composition at or in close proximity to the interface between the composition and the contaminated surface. This enables the organisms to continue to attack and oxidise the hydrocarbon residues so that a very significant reduction in hydrocarbon concentration might be achieved.

In the case of contaminated surfaces which are inevitably subjected to washing, for example by the sea, the polymer content of the composition embodying the present invention impedes washing away from the contaminated surface of the organisms and of partially degraded hydrocarbons so that the organisms can continue to act on the contamination for a period much longer than would be achieved by the application of organisms and nutrient alone in aqueous solution. This is also important in a case where the sea or some other body of water is contaminated by oil. If the oil is floating, the composition embodying the present invention can be applied to the exposed surface of the oil. The polymeric constituent of the composition will assist the composition to adhere to the oil and thus maintain the organisms and enzymes released thereby in prolonged contact with the oil.

The composition may also be used to protect a surface against contamination. If the composition is applied to the surface, contaminants which settle on the composition subsequently will be degraded until they no longer adhere to the protective layer on the surface. This is useful in grease traps and in sewers. It will be understood that application of a composition incorporating suitable organisms to the wall of a sewer will reduce existing contamination of that wall.

In order to improve accessibility of the contaminant to the organisms and the enzymes produced thereby, there may be applied to the contaminant before there is applied the composition embodying the present invention a known solvent or dispersant for the contaminant.

In a case where the composition is applied to a contaminated surface at a substantially dry site, for example a wall of a building or rocks above high water level, water may be applied intermittently to the composition on the contaminated surface to maintain the activity of the organisms by ensuring that they do not dry out. Water may be conveniently applied by spraying.

The invention is useful in the removal of fats and grease from sewers. In some districts, considerable volumes of fats and grease accumulate on the walls of sewers and it is necessary to remove these accumulations. This can be achieved by introducing into the sewer a device which delivers an aqueous composition at a fairly high rate and at fairly low pressure through a spinning head which is moved along the sewer. The composition which is delivered by the spinning head breaks up the accumulation of fat so that this can float away in the aqueous composition which drains along the sewer. If the composition includes organisms useful in the degradation of fats, nutrients for the organisms and a thickening agent, the organisms will degrade the fat which has been released from the sewer wall.

Compositions embodying the present invention are also useful in fish farms. A composition embodying the invention can be used to treat the effluent from a fish farm to reduce the presence of pollutants, for example ammonia. In some situations, it is also desirable to reduce the presence of pollutants, for example ammonia, in water which flows to a chamber or pen containing fish. Again, the presence of a composition embodying the present invention in an inlet chamber can reduce the concentration of pollutants in water containing fish. A composition containing in the region 5% by weight of the thickening agent is useful in this way. The thickening agent helps to retain the organisms in an inlet chamber or in an outlet chamber and at least partly avoids the organisms being washed away from the fish farm.

In other situations where the discharge of organisms, for example into a lake or a stream, should be restricted, a composition embodying the present invention and which has a high viscosity, achieved by a sufficiently high proportion of the thickening agent, is useful for treating water to reduce pollution, whilst minimising the discharge of organisms in the treated water.

Compositions embodying the present invention are also useful in the biodegradation of oil in drilling mud. A composition embodying the invention may be introduced into drilling mud to achieve efficient degradation of hydrocarbons present in the mud.

The weight of organisms provided in the composition generally corresponds to a mass of the organisms, measured on a dry basis, which is within the range 0.1 milligramme to one kilogramme per liter of the aqueous composition. The nutrients for the organisms may comprise ammonium nitrate present in an amount from 0.01 g to 10 g per liter of the aqueous composition and a similar weight of a composition comprising nitrogen, phosphorous and potassium in the proportions 30:5:5.

Compositions embodying the present invention may include surfactants, additional enzymes, for example lipases, carbohydrases and proteases, sucrose or other sources of carbon, and additional nutrients for the organisms. These substances may be added to the aqueous composition which contains the thickening agent.

In some circumstances, a part or all of the hydroxypropylmethyl cellulose may be substituted by carboxymethyl cellulose. Carboxymethyl cellulose provides a more viscous aqueous composition for a given weight of polymer per liter of the composition. However, the composition may be more susceptible to precipitation in consequence of a reduction of the pH value of the composition and also may be more susceptible to the presence of ions in the composition. In some situations, the greater susceptibility of carboxymethyl cellulose to biodegradation, as compared with hydrroxypropylmethyl cellulose, renders the carboxymethyl cellulose less suitable as a thickening agent than is hydroxypropyl methyl cellulose.

The features disclosed in the foregoing description, or the following claims, or the accompanying drawings, expressed in their specific forms or in the terms or means for performing the desired function, or a method or process for attaining the disclosed result, may, separately or in any combination of such features, be utilised for realising the invention in diverse forms thereof.

I claim:

1. A method of alleviating contamination of a surface of an above-ground solid structure, which is contaminated by an organic contaminant, comprising applying to said surface an aqueous composition comprising (a) one or more selected organisms capable of degrading the contaminant, (b) nutrients selected to promote growth and reproduction of said organisms, and (c) a thickening agent which forms an air and water-permeable interface between the aqueous composition and the contaminant and serves to increase the viscosity of the aqueous composition and to restrict migration of the aqueous composition from the surface to which it has been applied.

2. A method according to claim 1 wherein the organic contaminant comprises hydrocarbons and the composition is not readily permeable to said hydrocarbons and the application of the composition to said surface restricts migration of said hydrocarbons from said surface.

3. A method of making an aqueous composition for use in the alleviation of contamination of a surface of an above-ground solid structure, which is contaminated by an organic contaminant, the composition comprising (a) one or more selected organisms capable of degrading the contaminant, (b) nutrient selected to promote growth and reproduction of said organisms, wherein the method is characterized by the step of adding to the aqueous composition, (c) a thickening agent which forms an air and water-permeable interface between the aqueous composition and the contaminant and serves to increase the viscosity of the aqueous composition and to restrict migration of the aqueous composition from a surface to which it is applied.

4. A method according to claim 3 wherein the thickening agent is a polymer which is dispersible in or soluble in water.

5. A method according to claim 3 wherein the thickening agent is an organic polymer.

6. A method according to claim 3 wherein the thickening agent is non-ionic.

7. A method according to claim 3 wherein the thickening agent is a polysaccharide.

8. A method according to claim 3 which comprises adding not more than 10% by weight of the thickening agent.

9. An aqueous composition for use in the alleviation of contamination of a surface of an above-ground solid structure, which is contaminated by an organic contaminant and comprising in combination (a) as an active component one or more selected organisms capable of degrading the contaminant, (b) nutrients selected to promote growth and reproduction of said organisms, and (c) a thickening agent which forms an air and water-permeable interface between the aqueous composition and the contaminant and serves to increase the viscosity of the aqueous composition and to restrict migration of the aqueous composition from a surface to which it is applied.

10. A composition according to claim 9 which is not readily permeable to hydrocarbons.

11. A composition according to claim 9 wherein the thickening agent is a polymer which is dispersible in or soluble in water.

12. A composition according to claim 9 wherein the thickening agent is an organic polymer.

13. A composition according to claim 9 wherein the thickening agent is non-ionic.

14. A composition according to claim 9 wherein the thickening agent is a polysaccharide.

15. A composition according to claim 9 which comprises not more than 10% by weight of the thickening agent.

* * * * *

UNITED STATES PATENT AND TRADEMARK OFFICE
CERTIFICATE OF CORRECTION

PATENT NO. : 5,821,113
DATED : October 13, 1998
INVENTOR(S) : Artur Haslimann

It is certified that error appears in the above-identified patent and that said Letters Patent is hereby corrected as shown below:

Column 2 Line 56 "he treated" should read --be treated--.

Signed and Sealed this

Twenty-seventh Day of July, 1999

Attest:

Q. TODD DICKINSON

*Attesting Officer*      *Acting Commissioner of Patents and Trademarks*